(12) United States Patent
Silva-Craig et al.

(10) Patent No.: US 7,386,462 B2
(45) Date of Patent: Jun. 10, 2008

(54) INTEGRATION OF RADIOLOGY INFORMATION INTO AN APPLICATION SERVICE PROVIDER DICOM IMAGE ARCHIVE AND/OR WEB BASED VIEWER

(75) Inventors: Milton Silva-Craig, Arlington Heights, IL (US); Greg Angst, Cary, IL (US); Thanos Karras, Mount Prospect, IL (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 1063 days.

(21) Appl. No.: 09/681,311

(22) Filed: Mar. 16, 2001

(65) Prior Publication Data

US 2002/0133373 A1 Sep. 19, 2002

(51) Int. Cl.
G06Q 10/00 (2006.01)
G06Q 50/00 (2006.01)
A61B 5/00 (2006.01)
G06F 19/00 (2006.01)

(52) U.S. Cl. .............................. 705/2; 705/3; 382/128
(58) Field of Classification Search .................... 705/2, 705/3; 382/128
See application file for complete search history.

(56) References Cited

U.S. PATENT DOCUMENTS

| | | | |
|---|---|---|---|
| 6,078,925 A * | 6/2000 | Anderson et al. ........ | 707/103 R |
| 6,260,021 B1 * | 7/2001 | Wong et al. .................... | 705/2 |
| 6,429,878 B1 * | 8/2002 | Turek et al. ................. | 345/636 |
| 6,678,703 B2 * | 1/2004 | Rothschild et al. .......... | 707/201 |
| 6,823,203 B2 * | 11/2004 | Jordan ......................... | 600/407 |
| 6,904,161 B1 * | 6/2005 | Becker et al. .............. | 382/128 |
| 7,010,144 B1 * | 3/2006 | Davis et al. ................. | 382/100 |
| 7,027,633 B2 * | 4/2006 | Foran et al. ................. | 382/133 |
| 2002/0091659 A1 * | 7/2002 | Beaulieu et al. .............. | 706/62 |
| 2003/0130786 A1 * | 7/2003 | Ilkin et al. ................... | 701/205 |

OTHER PUBLICATIONS

Kohn, Imaging world shows DICOM standard works, Mar. 1995, Health Management Technology, pp. 20-24.*

* cited by examiner

*Primary Examiner*—C. Luke Gilligan
(74) *Attorney, Agent, or Firm*—McAndrews, Held & Malloy, Ltd.; Peter J. Vogel; Michael A. Dellapenna (57) ABSTRACT

A preferred embodiment of the present invention provides a method and apparatus for integration of radiology information into an Application Server Provider DICOM Image Archive and/or Web Based Viewer. A preferred embodiment includes a medical information source that includes medical information in a medical information format, a medical image source that includes medical images in a medical image format, a data center for storing medical images and medical information in at least one format, and an interface for transmitting images and medical information between the medical information source and the medical image source and the data center. In a preferred embodiment, the interface simultaneously transmits both medical images and medical information in different formats.

28 Claims, 4 Drawing Sheets

INTEGRATION OF RADIOLOGY INFORMATION INTO AN APPLICATION SERVICE PROVIDER DICOM IMAGE ARCHIVE AND/OR WEB BASED VIEWER

BACKGROUND OF INVENTION

The preferred embodiments of the present invention generally relate to centralized medical information systems, and in particular relate to a method and system for integration of radiology information into an Application Server Provider (ASP) DICOM Image Archive (Archive) and/or Web Based Viewer (Viewer).

Medical images improve diagnosis and/or treatment of patients by healthcare professionals by helping healthcare professionals to identify and locate problems in a patient (such as fractures, foreign objects, tumors, etc.), for example. Medical reports and other data (such as radiology information, for example) further improve effective and accurate patient diagnosis and treatment by providing supplemental information such as the size of a foreign object, patient chemical levels, patient history, bone density, and/or other patient data, for example.

Some healthcare facilities (such as hospitals, clinics, doctors' offices, or other medical offices) maintain on site databases to store medical images. Typically, such an on site database of images is called a Picture Archiving and Communication System (PACS). A PACS may be used, for example, to obtain, store, and distribute electronic images, such as medical images. Additionally, a PACS may allow images to be archived in electronic form in a central location on site. A PACS may also allow images to be shared among different users because the images are locally centralized and able to be accessed at numerous points on site. Convenient access to patient data through a PACS may improve individual hospital workflow by eliminating the need to physically transfer images and by providing multiple viewing stations for imaging results.

Typically, data stored in a PACS is stored as DICOM data. DICOM stands for Digital Imaging and Communications in Medicine. DICOM is a standard for image and information transmission. DICOM relates to the transfer of electronic data between medical diagnostic and imaging systems. The DICOM protocol may be employed in communication between medical devices and PACS. The DICOM standard enumerates a command set, data formats, interface specifications, communication protocols, and command syntax. However, the DICOM standard does not specify details of implementation. DICOM sets forth Information Objects (types of data, such as computerized tomography, magnetic resonance, x-ray, ultrasound, etc.), Service Classes (actions with data, such as send, receive, print, etc.), and data transmission protocols. The Service Class User (SCU) protocol governs use of the DICOM service. The Service Class Provider (SCP) protocol governs the provider of the DICOM service.

Some healthcare facilities also maintain clinical information systems for clinical reports and other medical or administrative information. As an example, a Hospital Information System (HIS) may include a Financial Information System (FIS), a Pharmacy Information System (PIS), and/or a Radiology Information System (RIS), for example. A Radiology Information System (RIS) includes radiology information for patients examined. Radiology information may include radiology reports, messages, warnings, alerts, patient scheduling information, patient demographic data, patient tracking information, and physician and patient status monitors, as examples. A RIS may also allow order entry and tracking of images and film. A HIS may be used by any healthcare facility, such as a hospital, clinic, doctor's office, or other medical office.

Typically, clinical information systems communicate using the HL-7 (Health Level Seven) protocol. HL-7 is an ANSI (American National Standards Institute) accredited standard establishing interface requirements and communication protocols, including a message format for communication and data transfer. Typically, clinical reports from clinical information systems such as hospital information systems, for example, are in HL-7 format. The HL-7 format for clinical reports is not directly compatible with the DICOM format for images.

Currently, clinical information systems are typically located on site at individual healthcare facilities. Current methods for transferring images and medical information between healthcare facilities rely on physical transfer such as postal mail or courier.

Typically, individual healthcare facilities have access to only their databases and not the databases of other facilities. Thus, the localized nature of clinical databases limits a patient's choice of healthcare facility and limits the sharing of information. Thus, there is a need for a method of centralized access to images and medical data.

Application Service Providers (ASPs) have been employed in the field of computers to allow for centralization of data. ASPs operate as hosts for data and applications. Typically, ASPs maintain applications and data in an off-site data center. ASPs have been hired by companies in the field of computers to manage data and computer applications. Companies may access data and applications via an ASP. Typically, in the computer field, companies remotely access data and applications via an ASP central data location.

In the field of computers, ASPs offer several desirable services, such as secure data storage, data backup, and redundant systems. Because ASPs offer such services, a customer of an ASP may not have to incur additional expenses for its own security, backup, and storage systems. In addition to functioning as a remote database, ASPs may host a number of applications that may be activated or accessed remotely by customers. By concentrating computing power and maintenance at the ASP, the ASP may offer continuous access to and support of the applications and alleviate the need for the customer to purchase and maintain its own expensive computer equipment.

For example, ASPs may provide installation, management, and support of applications and storage of data to many remote clients. Client data may be stored at a remote data center. Data may be retrieved from a remote data center via a communications medium such as the Internet or a private network. Additionally, ASPs may deliver applications such as email systems, resource planning systems, customer relationship management systems, human resource management systems, and proprietary applications to remote clients.

As described above, it is currently difficult to transfer patient images and reports between healthcare facilities due to the localized nature of the on site databases. Typically, films and reports are manually transferred between facilities (often referred to as "sneaker net" in the art). Manual transfer is inefficient because it wastes time, money, and human resources. Additionally, the separation of DICOM image data and HL-7 clinical reports due to incompatible formats increases hospital computing resource usage due to the need for separate systems. Centralized access to both images and clinical data may improve the workflow of a healthcare facility by providing a single storage system and a single viewing system rather than separate systems for images and for clinical reports. Integrated access to images and clinical reports may allow for improved diagnosis and treatment of patients through fast, comprehensive access to both images and supporting clinical data.

Thus, a need exists for linking images and clinical reports in a single database. Additionally, there is a need for remote access to images and clinical reports at multiple sites. There is a further need for more efficient transmission of images and clinical reports and for simultaneous transmission of images and clinical reports. There is also a need for centralized storage of images and clinical reports in an application service provider. There is a need for access to images and clinical reports via an application service provider.

SUMMARY OF INVENTION

A preferred embodiment of the present invention provides a method and system for integration of radiology information into an Application Service Provider DICOM Image Archive and/or Web Based Viewer. A preferred embodiment includes a medical information source that includes medical information in a medical information format, a medical image source that includes medical images in a medical image format, a data center for storing medical images and medical information in at least one format, and an interface for transmitting images and medical information between the medical information source and the medical image source and the data center. In a preferred embodiment, the interface simultaneously transmits both medical images and medical information in different formats. The data center may include an archive for storing medical images and medical information and a viewer for allowing access to medical images and medical information. In a preferred embodiment, the medical image source is a Picture Archiving and Communications System or medical diagnostic imaging system. In a preferred embodiment, the medical information source is a hospital information system (such as a radiology information system, for example). In a preferred embodiment, the data center also includes an external access interface for allowing users to access medical images and medical information at the data center.

In a preferred embodiment, the method includes converting the medical information from a first format into a second format compatible with the medical image format. Then, in a preferred embodiment, the method includes transmitting the converted medical information with the medical image to a data center. Finally, the method includes storing the converted medical information with the medical image in the data center. The medical information and medical image may be retrieved by a user. Preferably, the user accesses the data center via a web browser, DICOM viewing workstation, or other such access device.

DETAILED DESCRIPTION

Figure 1:
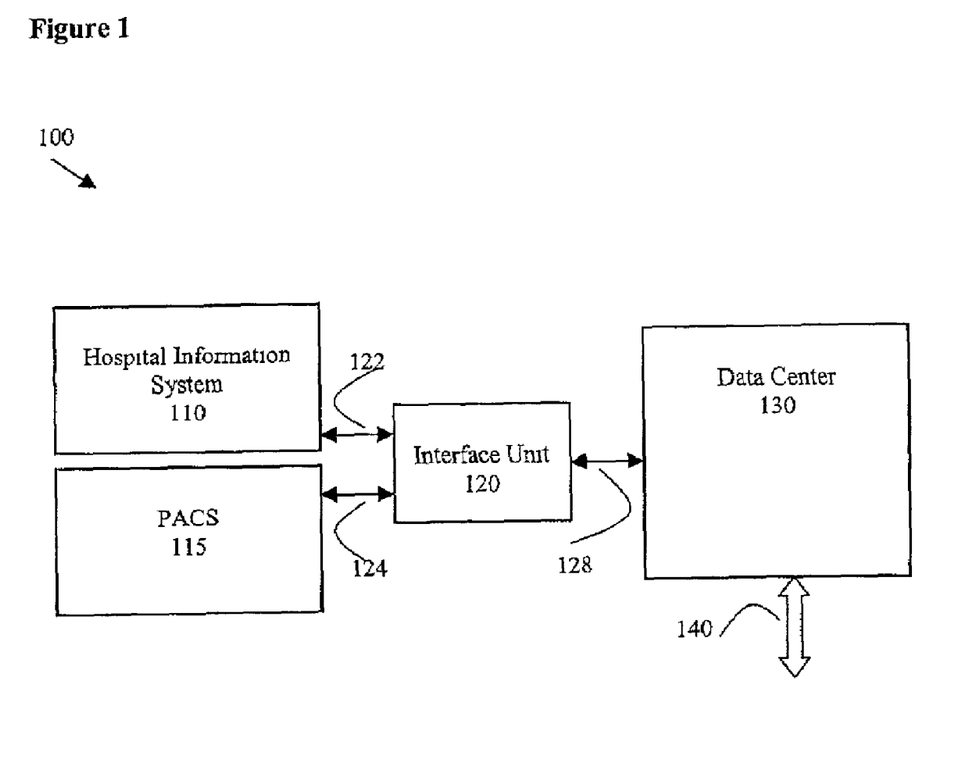
FIG. 1 illustrates a medical information system used in accordance with a preferred embodiment of the present invention.

FIG. 1 illustrates a medical information system 100 used in accordance with a preferred embodiment of the present invention. The medical information system 100 includes a plurality of subsystems, such as a hospital information system 110, a PACS (Picture Archiving and Communication System) 115, an interface unit 120, a data center 130, and an external access interface 140. The interface unit 120 includes a hospital information system interface connection 122, a PACS interface connection 124, and a data center interface connection 128. The interface unit 120 facilitates communication between the hospital information system 110, the PACS 115, and the data center 130. The external access interface 140 allows access by entities, such as healthcare facilities (for example, a hospital, clinic, doctor's office, other medical office, or terminal) to the data center 130.

The hospital information system 110 stores medical information such as clinical reports, patient information, radiology information, and/or administrative information, as examples, but typically not images. In a preferred embodiment, the hospital information system 110 is housed in a healthcare facility. In a preferred embodiment, the hospital information system 110 includes a radiology information system. The radiology information system stores information such as radiology reports, messages, warnings, alerts, patient scheduling information, patient demographic data, patient tracking information, and/or physician and patient status monitors, for example. The radiology information system may also allow exam order entry (for example, ordering an x-ray of a patient) and image and film tracking (for example, tracking who has checked out a film). In a preferred embodiment, information in the radiology information system is formatted according to the HL-7 (Health Level Seven) clinical communication protocol. Preferably, information is input in the hospital information system 110 by healthcare practitioners (such as radiologists, physicians, or technicians, for example) before or after patient examination.

The PACS 115 preferably stores medical images. Preferably, the PACS 115 stores images as digital images. Typically, images are stored in the PACS 11S using the DICOM (Digital Imaging and Communications in Medicine) format. In a preferred embodiment, the PACS 115 is housed in a healthcare facility. Preferably, the PACS 115 is a local archive. Preferably, images are stored in the PACS 115 by healthcare practitioners (such as imaging technicians, physicians, radiologists, for example) after a medical imaging of a patient or are automatically transmitted from medical imaging devices. Preferably, the PACS 115 may also be a display device or viewing workstation, for example.

In a preferred embodiment, the data center 130 is an archive, storing information such as images, data, and/or reports, for example. Preferably, the data center 130 may also serve as a central conduit to information located at other sources, such as local archives, hospital information systems/radiology information systems (HIS/RIS), or medical imaging systems, for example. That is, the data center 130 may store links or indicators (such as identification numbers, patient names, or record numbers, for example) to information. In a preferred embodiment, the data center 130 is managed by an application server provider (ASP). In a preferred embodiment, the data center 130 is located in a centralized location that may be accessed by many systems and facilities (such as hospitals, clinics, doctor's offices, other medical offices, or terminals). The data center 130 may be spatially distant from the hospital information system 110 and the PACS 115 (for example, GE headquarters). Preferably, the interface unit 120 allows the data center 130 to communicate with the hospital information system 110 and the PACS 115. The external access interface 140 allows the data center 130 to communicate with entities such as healthcare facilities, computer systems, and the like. In a preferred embodiment, the external access interface 140 is a network, such as the Internet or a private network, for example. In an alternative embodiment, the interface unit 120 may include the external access interface 140.

The interface unit 120 allows communication between the data center 130, the hospital information system 110, and the PACS 115. Preferably, the interface unit 120 uses a network (preferably, a Wide Area Network (WAN) such as a private network or the Internet, for example) to communicate between the hospital information system 110 and the PACS 115 and the data center 130. In a preferred embodiment, the interface unit 120 also includes a broker (such as Mitra Imaging's PACS Broker) to allow medical information and medical images to be transmitted together and stored together. Preferably, the hospital information system interface connection 122 of the interface unit 120 is a network (preferably, a WAN such as a private network or the Internet, for example). Additionally, the PACS interface connection 124 is preferably a network such as a private network or the Internet, for example. The data center interface connection 128 is also preferably a network such as a private network or the Internet, for example. Preferably, the hospital information system 110 and the PACS 115 may communicate with the data center 130 via the interface unit 120. Additionally, the hospital information system 110 preferably may communicate with the PACS 115 via the interface unit 120.

In operation, in a preferred embodiment, the interface unit 120 receives images from the PACS 115 via the PACS interface connection 124. Preferably, the images are received in a medical image format, such as DICOM format, for example. Additionally, the interface unit 120 receives medical information (such as clinical reports, medical information, and/or administrative information, for example) from the hospital information system 110 via the hospital information system interface connection 122. Preferably, the medical information is received in a medical information format, such as HL-7 format, for example. However, the medical information format (for example, HL-7) and the medical image format (for example, DICOM) are incompatible. The medical information may not be transmittable with the medical image format transmission protocol. Thus, the interface unit 120 then translates or reformats the medical information, such as reports, into a medical image format-compatible format, such as SQL (Structured Query Language) database format or a standard text format, for example. Preferably, the reformatted medical information may be transmitted using the medical image format transmission protocol. Preferably, the medical image and the reformatted medical information share common identification elements, such as patient name, which enable the reformatted medical information to be associated with the medical image.

Next, the interface unit 120 transmits the images and the medical information to the data center 130 via the data center interface connection 128. Finally, medical information is preferably stored in the data center 130 in medical image format compatible-format, such as SQL format, together with images in medical image format, such as DICOM format. That is, in a preferred embodiment, the interface unit 120 allows the medical image and medical information to be transmitted and stored together. Additionally, the medical image and medical information may be transmitted separately via the interface unit 120. Preferably, the medical image and medical information are later viewable and easily retrievable, such as by their common identification element (such as patient name or record number, for example).

Figure 2:
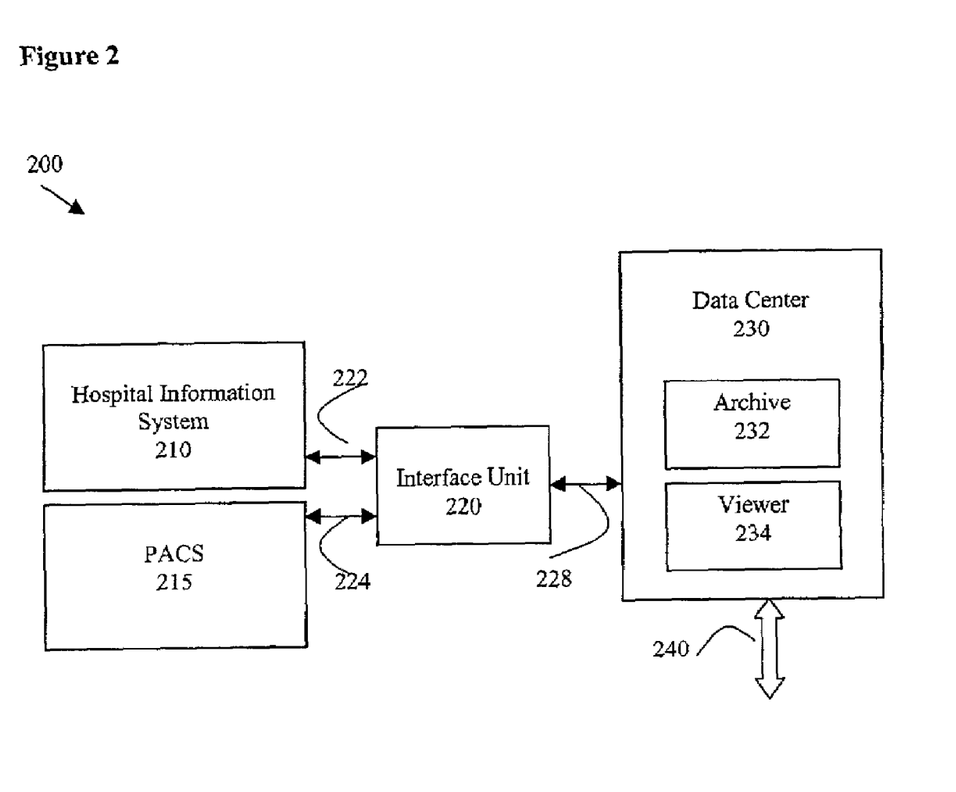
FIG. 2 illustrates a medical information system used in accordance with a preferred embodiment of the present invention.

FIG. 2 illustrates a medical information system 200 used in accordance with a preferred embodiment of the present invention. The medical information system 200 includes a plurality of subsystems, such as a hospital information system 210, a PACS 215, an interface unit 220, a data center 230, and an external access interface 240. The data center 230 includes an archive 232 and a viewer 234. The interface unit 220 includes a hospital information system interface connection 222, a PACS interface connection 224, and a data center interface connection 228. As described above in reference to FIG. 1, the interface unit 220 allows the data center 230 to communicate with the hospital information system 210 and the PACS 215. As described above in reference to FIG. 1, the external access interface 240 allows access by entities, such as healthcare facilities, to the data center 230.

The hospital information system 210 is substantially similar to the hospital information system 110 described above in reference to FIG. 1. The hospital information system 210 stores medical information such as clinical reports, patient information, radiology information, and/or administrative information in a medical information format, for example, in HL-7 format. Preferably, the hospital information system 210 is housed in a healthcare facility. Preferably, information is input in the hospital information system 210 by healthcare practitioners (such as radiologists, physicians, technicians, for example) before or after patient examination.

The PACS 215 is substantially similar to the PACS 115 described above in reference to FIG. 1. Preferably, the PACS 215 stores medical images in a medical image format, such as DICOM format, for example. Preferably, the PACS 215 is housed in a healthcare facility. Preferably, images are stored in the PACS 215 by healthcare practitioners (such as imaging technicians, physicians, radiologists, for example) after medical imaging of a patient or by automatic transmittal from medical imaging devices.

In a preferred embodiment, the data center 230 includes an archive 232 for storing information such as images, data, and/or reports, for example. Preferably, the data center 230 may also serve as a conduit to information in other locations. For example, the data center 230 may store links to information in other locations. The data center 230 also includes a viewer 234. Preferably, the viewer 234 is a web server that allows access to ("serves up") information via a web browser, a terminal, or other such information access system. The viewer 234 may serve up information from the archive 232 through the external access interface 240 for access by users with web browsers, for example. The viewer 234 may also serve up information from the hospital information system 210 and/or the PACS 215. In a preferred embodiment, the data center 230 is managed by an application server provider (ASP). In a preferred embodiment, as described above in relation to FIG. 1, the data center 230 is located in a centralized location that may be accessed by many systems and facilities. Additionally, the data center 230 may be located spatially distant from the healthcare information facility 210 and the PACS 215.

As described above with reference to FIG. 1, the interface unit 220 allows communication between the data center 230, the hospital information system 210, and the PACS 215. The external access interface 240 allows communication with entities such as computer systems and/or healthcare facilities, for example. In a preferred embodiment, as described above with reference to FIG. 1, the external access interface 240 is a network, such as the Internet or a private network, for example. As described above, the external access interface 240 may be included in the interface unit 220.

The interface unit 220 is substantially similar to the interface unit 120 described above with reference to FIG. 1 in the path from the hospital information system 210 and the PACS 215 to the data center 230. Additionally, the interface unit 220 also allows communication from the data center 230 to the hospital information system 210 and the PACS 215. The interface unit 220 also allows communication between the hospital information system 210 and the PACS 215. The interface unit 220 allows transmission of medical images and medical information as described above with reference to FIG. 1. The interface unit 220 may receive images in a medical image format, preferably in DICOM format, from the PACS 215 via the PACS interface connection 224. Additionally, the interface unit 220 may receive medical information in a medical information format, preferably in HL-7 format, from the hospital information system 210 via the hospital information system interface connection 222. Then, the interface unit 220 translates the medical information from the medical information format, such as HL-7 format, into a medical image format-compatible format, such as SQL format or a standard text format. Thus, as described above in relation to FIG. 1, the medical information may be transmitted according to the medical image protocol. Additionally, as described above, the medical information may be associated with the medical image. Next, the interface unit 220 transmits the images and the medical information to the data center 230 via the data center interface connection 228. Preferably, the interface unit 220 may transmit medical images and medical information together to the data center 230. Additionally, the interface unit 220 may preferably transmit medical images and medical information individually to the data center 230 (such as at separate times or along separate lines of communication, for example). Finally, the medical information is preferably stored in the archive 232 in medical image format-compatible format together with images in medical image format. Alternatively, the medical image is stored in the archive 232 along with a link to the medical information at the hospital information system 210. Alternatively, the medical information may be stored in the archive 232 in medical image format-compatible format together with a link to the medical image in the PACS 215.

Preferably, when a user accesses the viewer 234 via the external access interface 240 and requests an image and/or medical information (such as by using a signal or a command, for example), the viewer 234 retrieves the images and/or medical information from the archive 232. The user may view the requested images and/or medical information via the viewer 234. Preferably, the user views the requested images and/or medical information via the viewer 234 using a web browser, DICOM viewing station, or other such access device.

In an alternative embodiment, when a user accesses the viewer 234 via the external access interface 240 and requests an image and medical information, the viewer 234 retrieves the requested image from the archive 232. Additionally, the viewer 234 retrieves the requested medical information (such as radiology information) from the hospital information system 210 using the interface unit 220.

Preferably, the medical information is temporarily stored at the viewer 234 for the user's access.

In another embodiment, instead of retrieving images and/or medical information from the data center 230, images and/or medical information may be retrieved directly from the hospital information system 210 and/or the PACS 215. That is, when a user accesses the viewer 234 via the external access interface 240 and requests an image and/or medical information, the viewer 234 retrieves the requested image from the PACS 215 using the interface 220 and/or retrieves the requested information from the hospital information system 210 using the interface unit 220. The interface unit 220 translates the requested medical information as described above. Preferably, the image and/or medical information are temporarily stored at the viewer 234 for the user's access.

Figure 3:
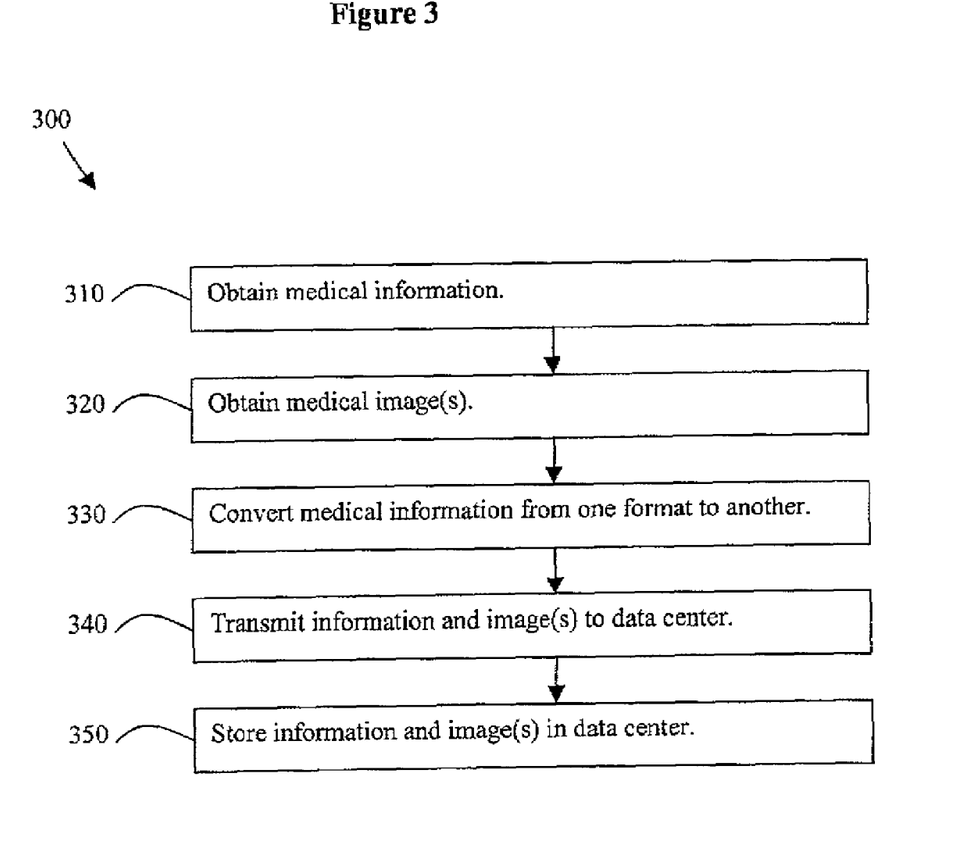
FIG. 3 illustrates a flowchart for integrating medical information into an image archive in accordance with a preferred embodiment of the present invention.

FIG. 3 illustrates a flowchart 300 for integrating medical information into an image archive in accordance with the medical information system 100 of FIG. 1. First, at step 310, medical information, such as radiology information (patient name, accession number, referring physician, radiology reports, as examples), administrative information, or other clinical information, for example, is obtained from a patient. Preferably, the medical information is obtained by a healthcare practitioner (such as a physician, radiologist, or technician, for example). Alternatively, the medical information may be recorded by medical diagnostic equipment. Preferably, the medical information is formatted according to a medical information format, such as HL-7 format.

Next, at step 320, at least one medical image (such as a computerized tomography image, x-ray image, ultrasound image, magnetic resonance image, for example) is obtained of a patient. Preferably, the medical image is obtained using medical diagnostic imaging equipment (such as an x-ray system, ultrasound system, computerized tomography system, magnetic resonance imaging system, for example). Preferably, the medical image is formatted according to a medical image format, such as DICOM format.

Then, at step 330, the medical information is converted from the medical information format, such as HL-7 format, for example, to a medical image format-compatible format, such as SQL format or a standard text format, for example. Next, at step 340, the converted medical information is transmitted along with at least one medical image to the data center 130. Finally, at step 350, the medical information and medical image(s) are stored in the data center 130 for later retrieval by users (preferably, remote users).

Alternatively, the medical image(s) may be stored in the data center 130 along with a link to the medical information. Also, the medical information may be stored in the data center 130 with a link to the medical image(s). Additionally, links to the medical information and the medical image(s) may be stored at the data center 130 at step 350.

Figure 4:
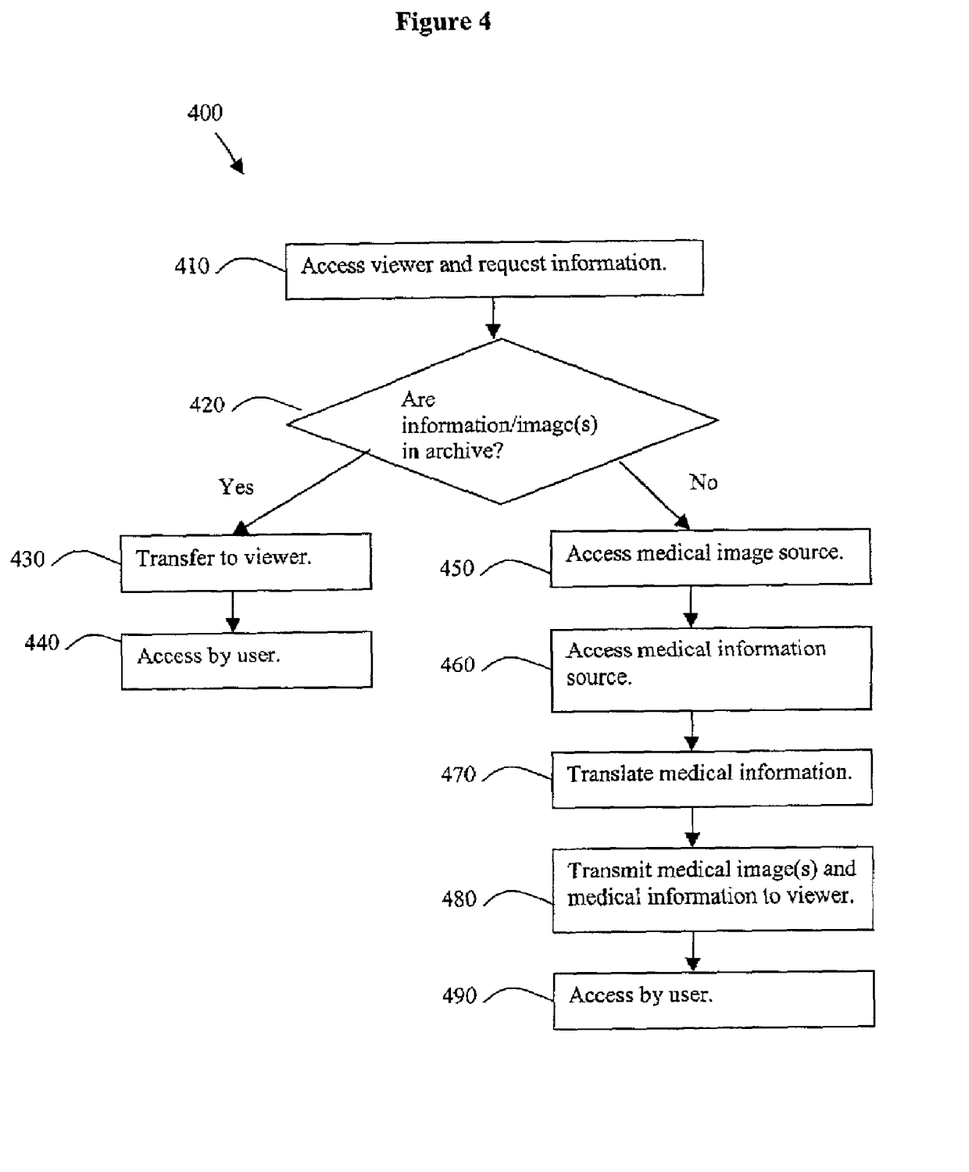
FIG. 4 illustrates a flowchart for accessing medical image(s) and medical information in accordance with a preferred embodiment of the present invention.

FIG. 4 illustrates a flowchart 400 for accessing medical images and medical information in accordance with the medical information system 200 of FIG. 2. Medical information and medical image(s) are stored in the data center 230 in a method substantially similar to the method described above in relation to FIG. 3. Alternatively, links to medical information and/or medical image(s) may be stored in the data center 230 in a method substantially similar to the method described above in relation to FIG. 3. Retrieval of medical information and medical image(s) by a user (preferably, a remote user) preferably proceeds according to the following steps. First, at step 410, a user accesses the viewer 234 of the data center 230 and requests medical information (such as radiology reports, patient demographic data, physician information, etc.) and medical image(s) (such as x-ray image(s), ultrasound image(s), magnetic resonance image(s), computerized tomography image(s), for example). Preferably, the user accesses the viewer 234 via a web browser, a DICOM viewing workstation, or other such information access system. Next, at step 420, the viewer 234 accesses the archive 232 of the data center 230. If the requested medical information and medical image(s) are found in the archive 232, then, at step 430, the archive 232 transfers the requested medical information and medical image(s) to the viewer 234. Preferably, the requested medical information and medical image(s) are temporarily stored at the viewer 234. Then, at step 440, the user may access the requested medical information and medical image(s) at the viewer 234, preferably using a web browser, terminal, or other such information access system.

If the requested medical information and medical image(s) are not found in the archive 232, then, at step 450, the viewer 234 accesses a medical image source (such as a PACS 215, for example) via the interface unit 220 and requests the requested medical image(s). Next, at step 460, the viewer 234 accesses a medical information source (such as the hospital information system 210, for example) and requests the request medical information. Then, at step 470, the interface unit 220 translates the medical information from a medical information format (such as HL-7 format, for example) to a medical image format-compatible format (such as SQL or a standard text format, for example). Then, at step 480, the translated medical information in a medical image format-compatible format is transmitted with the medical image(s) in a medical image format (such as DICOM format) to the viewer 234 via the interface unit 220. Preferably, the medical information and medical image(s) are temporarily stored in the viewer 234. Finally, at step 490, the user may access the requested medical information and medical image(s) at the viewer 234, preferably using a web browser, terminal, or other such information access system.

In an alternative embodiment, the medical information or the medical image(s) may be found in the archive 232. Then, the medical information or the medical image (s) in the archive 232 is retrieved from the archive 232. Next, the medical information or the medical image(s) not found in the archive 232 are retrieved from the hospital information system 210 or the PACS 215 via the interface unit 220 according to the methods described above. Then, the medical information and medical images(s) may be displayed at the viewer 234.

Thus, the preferred embodiments allow medical images and patient and/or medical report data to be transmitted, stored, and viewed together. Additionally, the preferred embodiments provide centralized storage of medical images and medical information and allow access to stored medical images and medical information via multiple access points. Because of the multiple access points, the preferred embodiments allow healthcare facilities and healthcare practitioners to share and compare data and images in various locations. Also, the preferred embodiments allow relatively immediate access to examination images and data independent of location.

Thus, the preferred embodiments of the present invention provide many important advantages. The preferred embodiments provide an advantage by allowing the combination of medical image and medical information storage and transmission systems. The preferred embodiments provide a further advantage by allowing more efficient information sharing between a plurality of healthcare facilities and healthcare practitioners. The preferred embodiments provide more efficient use of time, money, and personnel by healthcare facilities and healthcare practitioners through centralized access to medical images and medical information.

While the invention has been described with reference to a preferred embodiment, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A medical information system, said system comprising:
a medical information source, said medical information source providing medical information in a medical information format;
a medical image source, said medical image source providing medical images in a medical image format;
an interface unit adapted to receive said medical information, wherein said interface unit is adapted to automatically translate said medical information into a medical image format-compatible format in response to receiving said medical information, wherein said interface unit is adapted to receive said medical image, wherein said interface unit is adapted to automatically create associated medical data including at least one of a link to said medical information and said medical information in said medical image format-compatible format associated with at least one of a link to said medical image and said medical image in response to automatically translating said medical information, and transmitting said associated medical data, said medical image and medical information associated for transmission as associated medical data in said medical-image format compatible format based on a common identification element; and
a data center receiving said associated medical data and storing for later retrieval said associated medical data including at least one of a link to said medical information and said medical information associated with at least one of a link to said medical image and said medical image.

2. The system of claim 1, wherein said data center comprises an archive for storing medical images and medical information.

3. The system of claim 1, wherein said data center comprises a viewer for allowing access to medical images and medical information.

4. The system of claim 1, wherein said medical image source comprises a picture archiving and communications system.

5. The system of claim 1, wherein said medical information source comprises a hospital information system.

6. The system of claim 1, wherein said medical information source comprises a radiology information system.

7. The system of claim 1, wherein said data center comprises an application service provider.

8. The system of claim 1, wherein said data center further comprises an external access interface for allowing users to access medical images and medical information at said data center.

9. The system of claim 1, wherein said medical information comprises radiology information.

10. The system of claim 1, wherein said interface comprises a broker for translating said medical information format.

11. The system of claim 10, wherein said broker translates from Health Level Seven format to Structured Query Language format.

12. The system of claim 1, wherein said data center comprises a web server for allowing access to medical images and medical information via at least one web browser.

13. The system of claim 1, wherein said data center comprises a DICOM viewing workstation for allowing access to medical images and medical information.

14. The system of claim 1, wherein said data center further stores links to said medical information.

15. The system of claim 1, wherein said data center further stores links to said medical image.

16. The system of claim 1, wherein said interface unit transmits a link representing the location of said medical information.

17. The system of claim 1, wherein said interface unit transmits a link representing the location of said medical image.

18. A centralized medical information system, said system comprising:

an interface unit adapted to receive medical information from a medical information source in a medical information format, wherein said interface unit is adapted to automatically translate said medical information into a medical image format-compatible format in response to receiving said medical information, wherein said interface unit is adapted to receive a medical image from a medical image source in a medical image format, wherein said interface unit is adapted to automatically create associated medical data including at least one of a link to said medical information and said medical information in said medical image format-compatible format associated with at least one of a link to said medical image and said medical image in response to automatically translating said medical information, and transmitting said associated medical data, said medical image and medical information associated for transmission as associated medical in said medical-image format compatible format data based on a common identification element; and a data center receiving said associated medical data and storing for later retrieval said associated medical data including at least one of a link to said medical information and said medical information associated with at least one of a link to said medical image and said medical image.

19. The system of claim 18, wherein said data center comprises an archive for storing medical images and medical information.

20. The system of claim 18, wherein said data center comprises a viewer for allowing access to medical images and medical information.

21. The system of claim 18, wherein said data center comprises an application service provider.

22. The system of claim 18, wherein said data center further comprises an external access interface for allowing users to access medical images and medical information at the data center.

23. The system of claim 18, wherein said medical information comprises radiology information.

24. The system of claim 18, wherein said interface unit comprises a broker for translating said medical information format.

25. The system of claim 24, wherein said broker translates from Health Level 7 format to Structured Query Language format.

26. The system of claim 18, wherein said data center comprises a web server for allowing access to medical images and medical information via web browsers.

27. The system of claim 18, wherein said interface unit transmits a link representing the location of said medical information.

28. The system of claim 18, wherein said interface unit transmits a link representing the location of said medical image.

* * * * *